United States Patent [19]

Welter et al.

[11] Patent Number: 4,550,168
[45] Date of Patent: Oct. 29, 1985

[54] BENZISOSELENAZOLONES AND A PROCESS FOR THE TREATMENT OF INFLAMMATORY DISEASES

[75] Inventors: André Welter; Sigurd Leyck, both of Pulheim; Eugen Etschenberg, Cologne, all of Fed. Rep. of Germany

[73] Assignee: A. Nattermann & Cie GmbH, Cologne, Fed. Rep. of Germany

[21] Appl. No.: 513,094

[22] Filed: Jul. 12, 1983

[30] Foreign Application Priority Data

Jul. 14, 1982 [DE] Fed. Rep. of Germany ....... 3226284

[51] Int. Cl.[4] .................. C07D 417/06; A61K 31/44; A61K 31/425; A61K 31/505
[52] U.S. Cl. .................................. 546/270; 544/333; 548/121; 548/159; 548/181; 548/209
[58] Field of Search .................... 546/270; 544/333; 548/181, 159, 121, 209, 241; 424/DIG. 4

[56] References Cited

U.S. PATENT DOCUMENTS

| | | | |
|---|---|---|---|
| 2,933,432 | 4/1960 | Lichtin | 424/DIG. 4 |
| 3,012,039 | 12/1961 | Morley | 548/209 |
| 4,156,729 | 5/1979 | Böshagen et al. | 548/209 |
| 4,243,669 | 1/1981 | Baggaley | 548/209 |
| 4,418,069 | 11/1983 | Welter | 548/121 |

FOREIGN PATENT DOCUMENTS 3027074 2/1982 Fed. Rep. of Germany ...... 548/121
3027075 2/1982 Fed. Rep. of Germany ...... 548/121

OTHER PUBLICATIONS

Chem. Abst., vol. 87, 117847u, Baggaley.
Chem. Abst., vol. 90, 204085z and 133026t, Beecham Group Ltd.
Slinger, Illinois Med. Journal, Mar. 1954.

Primary Examiner—Donald G. Daus
Assistant Examiner—Cecilia Shen
Attorney, Agent, or Firm—Pearne, Gordon, Sessions, McCoy, Granger & Tilberry

[57] ABSTRACT

The invention relates to new benzisoselenazolones of the general formula I

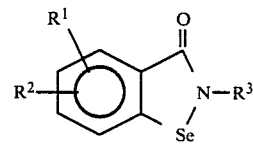

and a process for the treatment of humans suffering from inflammatory diseases of the rheumatic type.

11 Claims, No Drawings

BENZISOSELENAZOLONES AND A PROCESS FOR THE TREATMENT OF INFLAMMATORY DISEASES

The present invention relates to new benzisoselenazolones and a process for the treatment of humans by using them as active ingredients in medicaments for the treatment of inflammatory deseases of the rheumatic type.

The compounds according to the invention correspond to the formula I

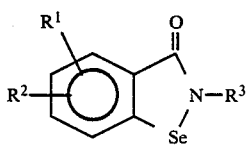

in which $R^1$ and $R^2$ can be identical or different and, independently of one another, denote hydrogen, halogen, $C_1$-$C_4$-alkyl, $C_1$-$C_4$-alkoxy, hydroxyl, trifluoromethyl, nitro, di-($C_1$-$C_4$-alkyl)-amino, or $R^1$ and $R^2$ together denote methylenedioxy, while $R^3$ denotes a heterocyclic unsaturated or saturated radical having 1 to 4 hetero atoms of the elements nitrogen and/or sulphur from the group comprising thiophenyl, thiazolyl, isothiazolyl, imidazolyl, pyrazolyl, thiadiazolyl, pyridyl, pyrimidinyl, pyrazinyl, pyridazinyl, benzothiacolyl, benzimidazolyl, benzotriazolyl, triazinyl, triazolyl, tetrazolyl, quinolinyl, isoquinolinyl, indolyl, indazolyl, carbazolyl, acridinyl, phenazinyl and pteridinyl, it being possible for the heterocyclic radical to be substituted once or twice, identically or differently, by halogen, $C_1$-$C_2$-alkyl, $C_1$-$C_4$-alkoxy, $C_1$-$C_4$-alkylthio, hydroxyl, mercapto, trifluoromethyl, nitro, phenyl, nitrile, carboxyl and/or $C_1$-$C_4$-alkoxy carbonyl. In this context, compounds in which $R^1$ and $R^2$ can be identical or different and, independently of one another, denote hydrogen, fluorine, chlorine, bromine, hydroxyl, methoxy, trifluoromethyl, nitro and/or methylenedioxy, while $R^3$ denotes a heterocyclic unsaturated or saturated radical having 1 to 4 hetero atoms of the elements nitrogen and/or sulphur from the group comprising the thiophenyl, thiazolyl, isothiazolyl, imidazolyl, pyrazolyl, thiadiazolyl, pyridyl, pyrimidinyl, pyrazinyl, pyridazinyl, benzothiazolyl, benzimidazolyl, triazinyl, triazolyl or tetrazolyl, it being possible for the heterocyclic radical to be substituted once or twice, identically or differently, by fluorine, chlorine, bromine, methyl, ethyl, butyl, methoxy, ethoxy, methylmercapto, ethylmercapto, hydroxyl, mercapto, trifluoromethyl, nitro, phenyl, nitrile, carboxyl and/or methoxycarbonyl and ethoxycarbonyl, are preferred.

Compounds in which $R^1$ and $R^2$ can be identical or different and, independently of one another, denote hydrogen, chlorine, methyl, methoxy, nitro and/or methylenedioxy, while $R^3$ denotes a heterocyclic unsaturated or saturated radical having 1 to 2 hetero atoms of the elements nitrogen and/or sulphur from the group comprising the thiophenyl, thiazolyl, pyridyl, pyrimidinyl, benzothiazolyl and benzimidazolyl, it being possible for the heterocyclic radical to be substituted once or twice, identically or differently, by fluorine, chlorine, bromine, methyl, methoxy, ethoxy, methylmercapto, hydroxyl, mercapto, nitrile, nitro, phenyl, carboxyl and/or methoxycarbonyl and ethoxycarbonyl, are particularly preferred.

Examples of compounds according to the invention are as follows:

2-(2-pyridyl)-1,2-benzisoselenazol-3(2H)-one,
2-(3-pyridyl)-1,2-benzisoselenazol-3(2H)-one,
2-(4-pyridyl)-1,2-benzisoselenazol-3(2H)-one,
6-methyl-2-(2-pyridyl)-1,2-benzisoselenazol-3(2H)-one,
6-chloro-2-(2-pyridyl)-1,2-benzisoselenazol-3(2H)-one,
6-methoxy-2-(pyridyl)-1,2-benzisoselenazol-3(2H)-one,
5-nitro-2-(2-pyridyl)-1,2-benzisoselenazol-3(2H)-one,
5-chloro-2-(pyridyl)-1,2-benzisoselenazol-3(2H)-one,
7-methoxy-2-(2-pyridyl)-1,2-benzisoselenazol-3(2H)-one,
6,7-methylenedioxy-2-(2-pyridyl)-1,2-benzisoselenazol-3(2H)-one,
2-(2-chloro-3-pyridyl)-1,2-benzisoselenazol-3(2H)-one,
2-(3-hydroxy-2-pyridyl)-1,2-benzisoselenazol-3(2H)-one,
2-(6-hydroxy-2-pyridyl)-1,2-benzisoselenazol-3(2H)-one,
2-(6-methoxy-3-pyridyl)-1,2-benzisoselenazol-3(2H)-one,
2-(3-nitro-2-pyridyl)-1,2-benzisoselenazol-3(2H)-one,
2-(5-nitro-2-pyridyl)-1,2-benzisoselenazol-3(2H)-one,
2-(3-methyl-2-pyridyl)-1,2-benzisoselenazol-3(2H)-one,
2-(4-methyl-2-pyridyl)-1,2-benzisoselenazol-3(2H)-one,
2-(5-methyl-2-pyridyl)-1,2-benzisoselenazol-3(2H)-one,
2-(6-methyl-2-pyridyl)-1,2-benzisoselenazol-3(2H)-one,
2-(3,5-dichloro-2-pyridyl)-1,2-benzisoselenazol-3(2H)-one,
2-(4,6-dimethyl-2-pyridyl)-1,2-benzisoselenazol-3(2H)-one,
2-(2,6-dichloro-3-pyridyl)-1,2-benzisoselenazol-3(2H)-one,
2-(5-chloro-2-pyridyl)-1,2-benzisoselenazol-3(2H)-one,
2-(4-chloro-2-pyridyl)-1,2-benzisoselenazol-3(2H)-one,
2-(4-carboxy-5-chloro-2-pyridyl)-1,2-benzisoselenazol-3(2H)-one,
2-(2-tetrahydropyridyl)-1,2-benzisoselenazol-3(2H)-one,
2-(3-carboxy-2-pyridyl)-1,2-benzisoselenazol-3(2H)-one,
2-(2-pyrimidinyl)-1,2-benzisoselenazol-3(2H)-one,
2-(4-methyl-2-pyrimidinyl)-1,2-benzisoselenazol-3(2H)-one,
2-(5-nitro-2-pyrimidinyl)-1,2-benzisoselenazol-3(2H)-one,
2-(4,6-dimethyl-2-pyrimidinyl)-1,2-benzisoselenazol-3(2H)-one,
2-(2,6-dimethyl-4-pyrimidinyl)-1,2-benzisoselenazol-3(2H)-one,
2-(5-ethoxy-2-ethylmercapto-4-pyrimidinyl)-1,2-benzisoselenazol-3(2H)-one,
2-(5-ethoxycarbonyl-2-hydroxy-4-pyrimidinyl)-1,2-benzisoselenazol-3(2H)-one,
2-(5-carboxy-4-pyrimidinyl)-1,2-benzisoselenazol-3(2H)-one,
2-(6-chloro-2-methylmercapto-4-pyrimidinyl)-1,2-benzisoselenazol-3(2H)-one,
2-(4-chloro-2-methylmercapto-6-pyrimidinyl)-1,2-benzisoselenazol-3(2H)-one,
2-(4-chloro-6-methyl-2-pyrimidinyl)-1,2-benzisoselenazol-3(2H)-one,
2-(6-chloro-3-nitro-2-pyrimidinyl)-1,2-benzisoselenazol-3(2H)-one,
2-(2-chloro-5-nitro-4-pyrimidinyl)-1,2-benzisoselenazol-3(2H)-one, 2-(4,6-dichloro-2-pyrimidinyl)-1,2-benzisoselenazol-3(2H)-one,
2-(4,6-dichloro-5-pyrimidinyl)-1,2-benzisoselenazol-3(2H)-one,
2-(4,6-dihydroxy-2-pyrimidinyl)-1,2-benzisoselenazol-3(2H)-one,
2-(2,6-dihydroxy-4-pyrimidinyl)-1,2-benzisoselenazol-3(2H)-one,
2-(2,4-dihydroxy-5-pyrimidinyl)-1,2-benzisoselenazol-3(2H)-one,
2-(4,6-dimercapto-2-pyrimidinyl)-1,2-benzisoselenazol-3(2H)-one,
2-(6-hydroxy-2-mercapto-4-pyrimidinyl)-1,2-benzisoselenazol-3(2H)-one,
2-(6-hydroxy-2-methylmercapto-4-pyrimidinyl)-1,2-benzisoselenazol-3(2H)-one,
2-(4-hydroxy-6-methyl-2-pyrimidinyl)-1,2-benzisoselenazol-3(2H)-one,
2-(2-hydroxy-5-methyl-4-pyrimidinyl)-1,2-benzisoselenazol-3(2H)-one,
2-(1-phenylpyrazolo(3,4-d)pyrimidin-4-yl)-1,2-benzisoselenazol-3(2H)-one,
2-(pyrazolo(3,4-d)pyrimidin-4-yl)-1,2-benzisoselenazol-3(2H)-one,
2-(6-hydroxypyrazolo(3,4-d)pyrimidin-4-yl)-1,2-benzisoselenazol-3(2H)-one,
2-(6-mercaptopyrazolo(3,4-d)pyrimidin-4-yl)-1,2-benzisoselenazol-3(2H)-one,
2-(2-hydroxy-4-pyrimidinyl)-1,2-benzisoselenazol-3(2H)-one,
2-(2-benzothiazolyl)-1,2-benzisoselenazol-3(2H)-one,
2-(4-chloro-2-benzothiazolyl)-1,2-benzisoselenazol-3(2H)-one,
2-(4-methoxy-2-benzothiazolyl)-1,2-benzisoselenazol-3(2H)-one,
2-(6-methoxy-2-benzothiazolyl)-1,2-benzisoselenazol-3(2H)-one,
2-(4-methyl-2-benzothiazolyl)-1,2-benzisoselenazol-3(2H)-one,
2-(2-methyl-5-benzothiazolyl)-1,2-benzisoselenazol-3(2H)-one,
2-(6-nitro-2-benzothiazolyl)-1,2-benzisoselenazol-3(2H)-one,
2-(6-bromo-2-benzothiazolyl)-1,2-benzisoselenazol-3(2H)-one,
2-(5,6-dimethyl-2-benzothiazolyl)-1,2-benzisoselenazol-3(2H)-one,
2-(6-ethoxy-2-benzothiazolyl)-1,2-benzisoselenazol-3(2H)-one,
2-(2-thiazolyl)-1,2-benzisoselenazol-3(2H)-one,
6-methyl-2-(2-thiazolyl)-1,2-benzisoselenazol-3(2H)-one,
6-chloro-2-(2-thiazolyl)-1,2-benzisoselenazol-3(2H)-one,
6-methoxy-2-(2-thiazolyl)-1,2-benzisoselenazol-3(2H)-one,
5-nitro-2-(2-thiazolyl)-1,2-benzisoselenazol-3(2H)-one,
5-chloro-2-(2-thiazolyl)-1,2-benzisoselenazol-3(2H)-one,
7-methoxy-2-(2-thiazolyl)-1,2-benzisoselenazol-3(2H)-one,
6,7-methylenedioxy-2-(2-thiazolyl)-1,2-benzisoselenazol-3(2H)-one,
2-(4-methyl-2-thiazolyl)-1,2-benzisoselenazol-3(2H)-one,
2-(5-nitro-2-thiazolyl)-1,2-benzisoselenazol-3(2H)-one,
2-(2-thiazolinyl)-1,2-benzisoselenazol-3(2H)-one,
2-(5-chloro-2-thiazolyl)-1,2-benzisoselenazol-3(2H)-one,
2-(3-methyl-5-isothiazolyl)-1,2-benzisoselenazol-3(2H)-one,
2-(2-imidazolyl)-1,2-benzisoselenazol-3(2H)-one,
2-(5-ethoxycarbonyl-2-imidazolyl)-1,2-benzisoselenazol-3(2H)-one,
2-(3-pyrazolyl)-1,2-benzimidazol-3(2H)-one,
2-(4-cyano-5-pyrazolyl)-1,2-benzisoselenazol-3(2H)-one,
2-(4-ethoxycarbonyl-3-pyrazolyl)-1,2-benzisoselenazol-3(2H)-one,
2-(4-ethoxycarbonyl-2-phenyl-3-pyrazolyl)-1,2-benzisoselenazol 3(2H)-one,
2-(4-cyano-3-pyrazolyl)-1,2-benzisoselenazol-3(2H)-one,
2-(2-phenyl-3-pyrazol-1,2-benzisoselenazol-3(2H)-one,
2-(1-phenyl-5-pyrazolon-3-yl)-1,2-benzisoselenazol-3(2H)-one,
2-(5-hydroxy-3-pyrazolyl)-1,2-benzisoselenazol-3(2H)-one,
2-(1,3,4-thiadiazol-2-yl)-1,2-benzisoselenazol-3(2H)-one,
2-(5-mercapto-1,3,4-thiadiazol-2-yl)-1,2-benzisoselenazol-3(2H)-one,
2-(5-methyl-1,3,4-thiadiazol-2-yl)-1,2-benzisoselenazol-3(2H)-one,
2-(5-trifluoromethyl-1,3,4-thiadiazol-2-yl)-1,2-benzisoselenazol-3(2H)-one,
2-(5-tert.-butyl-1,3,4-thiadiazol-2-yl)-1,2-benzisoselenazol-3(2H)-one,
2-(2-pyrazinyl)-1,2-benzisoselenazol-3(2H)-one,
2-(2-carboxy-3-pyrazinyl)-1,2-benzisoselenazol-3(2H)-one,
2-(2-pyridazinyl)-1,2-benzisoselenazol-3(2H)-one,
2-(2-benzimidazolyl)-1,2-benzisoselenazol-3(2H)-one,
2-(5,6-dimethyl-2-benzimidazolyl)-1,2-benzisoselenazol-3(2H)-one,
2-(5-benzotriazolyl)-1,2-benzisoselenazol-3(2H)-one,
2-(7-chloro-1,2,4-benzotriazin-3-yl)-1,2-benzisoselenazol-3(2H)-one,
2-(1,2,4-benzotriazin-3-yl)-1,2-benzisoselenazol-3(2H)-one,
2-(7-bromo-1,2,4-benzotriazin-3-yl)-1,2-benzisoselenazol-3(2H)-one,
2-(7-fluoro-1,2,4-benzotriazin-3-yl)-1,2-benzisoselenazol-3(2H)-one,
2-(7-nitro-1,2,4--benzotriazin-3-yl)-1,2-benzisoselenazol-3(2H)-one,
2-(2-benzothienyl)-1,2-benzisoselenazol-3(2H)-one,
2-(3-benzothienyl)-1,2-benzisoselenazol-3(2H)-one,
2-(2-thienyl)-1,2-benzisoselenazol-3(2H)-one,
2-(3-sulfolanyl)-1,2-benzisoselenazol-3(2H)-one,
2-(2,1,3-benzothiadiazol-4-yl)-1,2-benzisoselenazol-3(2H)-one,
2-(1,2,4-triazin-4-yl)-1,2,-benzisoselenazol-3(2H)-one,
2-(2,6-dimercapto-1,3,5-triazin-4-yl)-1,2-benzisoselenazol-3(2H)-one,
2-(5,6-dimethyl-1,2,4-triazin-3-yl)-1,2-benzisoselenazol-3(2H)-one,
2-(5,6-diphenyl-1,2,4-triazin-3-yl)-1,2-benzisoselenazol-3(2H)-one,
2-(1,2,4-triazol-4-yl)-1,2-benzisoselenazol-3(2H)-one,
2-(5-mercapto-1,2,4-triazol-3-yl)-1,2-benzisoselenazol-3(2H)-one,
2-(5-tetrazolyl)-1,2-benzisoselenazol-3(2H)-one,
2-(5-quinolyl)-1,2-benzisoselenazol-3(2H)-one, 2-(2-methyl-4-quinolyl)-1,2-benzisoselenazol-3(2H)-one,
2-(6-nitro-5-quinolyl)-1,2-benzisoselenazol-3(2H)-one,
2-(1,2,3,4-tetrahydroquinol-8-yl)-1,2-benzisoselenazol-3(2H)-one,
2-(2-quinolyl)-1,2,benzisoselenazol-3(2H)-one,
2-(3-quinolyl)-1,2-benzisoselenazol-3(2H)-one,
2-(8-quinolyl)-1,2-benzisoselenazol-3(2H)-one,
2-(6-methoxy-8-quinolyl)-1,2-benzisoselenazol-3(2H)-one,
2-(1-isoquinolyl)-1,2-benzisoselenazol-3(2H)-one,
2-(5-isoquinolyl)-1,2-benzisoselenazol-3(2H)-one,
2-(5-indolyl)-1,2-benzisoselenazol-3(2H)-one,
2-(5-isoindolyl)-1,2-benzisoselenazol-3(2H)-one,
2-(5-indazolyl)-1,2-benzisoselenazol-3(2H)-one,
2-(6-chloro-3-indazolyl)-1,2-benzisoselenazol-3(2H)-one,
2-(6-indazolyl)-1,2-benzisoselenazol-3(2H)-one,
2-(7-indazolyl)-1,2-benzisoselenazol-3(2H)-one,
2-(9-ethyl-3-carbazolyl)-1,2-benzisoselenazol-3(2H)-one,
2-(9-tetrahydroacridinyl)-1,2-benzisoselenazol-3(2H)-one,
2-(3-hydroxy-2-phenazinyl)-1,2-benzisoselenazol-3(2H)-one and
2-(4-hydroxy-2-pteridinyl)-1,2-benzisoselenazol-3(2H)-one.

The benzisoselenazolones of the formula I according to the invention can be used for the treatment of a large number of diseases, such as, for example, for the prophylaxis and therapy of infectious diseases, for stimulating the immune system or for selenium deficiency diseases, as defined by W. Kraus and P. Oehme, Das Deut. Gesundheitswesen, 1979, 34 (37), 1713–1718 and 1979, 34 (37), 1769–1773.

However, the benzisoselenazolones of the formula I are particularly distinguished by antiarteriosclerotic and antiinflammatory properties. They are particularly suitable for the therapy of rheumatic diseases, such as, for example, arthroses or chronic infective arthritis, the new compounds being distinguished by being very well tolerated because they are non-toxic and, in contrast to known antiinflammatory therapeutic agents, exhibit no ulcer formation or gastrointestinal irritation.

The new benzisoselenazolones of the formula I can be obtained in a manner known per se.

In this, an o-chloroselenobenzoyl chloride of the formula II

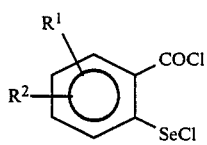

$R^1$ and $R^2$ having the meaning indicated in formula I, is reacted with a heterocyclic amine of the formula III

    III $R^3$ having the meaning indicated in formula I, under conditions of ring closure to give the benzisoselenazolones of the formula I.

The preparation of the appropriate o-chloroselenobenzoyl chlorides is carried out by the process of A. Ruwet and M. Renson, Bull. Soc. Chim. Belg. 1966, 75, 157–163.

Examples of suitable starting compounds of the formula II are the following compounds,
2-chloroselenobenzoyl chloride,
2-chloroseleno-4-chlorobenzoyl chloride,
2-chloroseleno-4-fluorobenzoyl chloride,
2-chloroseleno-4-methylbenzoyl chloride,
2-chloroseleno-4-methoxybenzoyl chloride,
2-chloroseleno-5-chlorobenzoyl chloride,
2-chloroseleno-5-methoxybenzoyl chloride,
2-chloroseleno-5-nitrobenzoyl chloride,
2-chloroseleno-3-methoxybenzoyl chloride and
2-chloroseleno-3,4-methylenedioxybenzoyl chloride.

Examples of suitable starting compounds III are the following:
2-amino-3-hydroxypyridine,
2-amino-6-hydroxypyridine,
5-amino-2-methoxypyridine,
2-amino-3-nitropyridine,
2-amino-5-nitropyridine,
2-amino-3-methylpyridine,
2-amino-4-methylpyridine,
2-amino-5-methylpyridine,
2-amino-6-methylpyridine,
2-aminopyridine,
3-aminopyridine,
4-aminopyridine,
2-amino-3,5-dichloropyridine,
2-amino-4,6-dimethylpyridine,
3-amino-2-chloropyridine,
2-amino-5-chloropyridine,
2-amino-4-chloropyridine,
3-amino-2,6-dichloropyridine,
2-amino-4-carboxy-5-chloropyridine,
2-aminotetrahydropyridine,
2-amino-3-carboxypyridine,
2-aminopyrimidine,
2-amino-4-methylpyrimidine,
2-amino-5-nitropyrimidine,
2-amino-4,6-dimethylpyrimidine,
4-amino-2,6-dimethylpyrimidine,
4-amino-5-ethoxycarbonyl-2-ethylmercaptopyrimidine,
4-amino-5-ethoxycarbonyl-2-hydroxypyrimidine,
4-amino-5-carboxypyrimidine,
4-amino-6-chloro-2-methylmercaptopyrimidine,
6-amino-4-chloro-2-methylmercaptopyrimidine,
2-amino-4-chloro-6-methylpyrimidine,
2-amino-6-chloro-3-nitropyrimidine,
4-amino-2-chloro-5-nitropyrimidine,
2-amino-4,6-dichloropyrimidine,
5-amino-4,6-dichloropyrimidine,
2-amino-4,6-dihydroxypyrimidine,
4-amino-2,6-dihydroxypyrimidine,
5-amino-2,4-dihydroxypyrimidine,
2-amino-4,6-dimercaptopyrimidine,
4-amino-6-hydroxy-2-mercaptopyrimidine,
4-amino-6-hydroxy-2-methylmercaptopyrimidine,
2-amino-4-hydroxy-6-methylpyrimidine,
4-amino-1-phenylpyrazolo(3,4-d)pyrimidine,
4-aminopyrazolo(3,4-d)-pyrimidine,
4-amino-6-hydroxypyrazolo(3,4-d)-pyrimidine,
4-amino-6-mercaptopyrazolo(3,4-d)pyrimidine,
4-amino-2-hydroxypyrimidine,
2-aminobenzothiazole,
2-amino-4-chlorobenzothiazole,
2-amino-4-methoxybenzothiazole,
2-amino-6-methoxybenzothiazole,
2-amino-4-methylbenzothiazole,
5-amino-2-methylbenzothiazole, 2-amino-6-nitrobenzothiazole,
2-amino-6-bromobenzothiazole,
2-amino-5,6-dimethylbenzothiazole,
2-amino-6-ethoxybenzothiazole,
2-aminothiophene,
3-aminosulfolane,
2-aminothiazole,
2-amino-4-methylthiazole,
2-amino-5-nitrothriazole,
2-amino-2-thiazoline,
2-amino-5-chlorothiazole,
5-amino-3-methylisothiazole,
2-aminoimidazole,
4-amino-5-ethoxycarbonylimidazole,
3-aminopyrazole,
5-amino-4-cyanopyrazole,
3-amino-4-ethoxycarbonylpyrazole,
3-amino-4-ethoxycarbonyl-2-phenylpyrazole,
3-amino-4-cyanopyrazole,
3-amino-2-phenylpyrazole,
3-amino-1-phenyl-5-pyrazolone,
3-amino-5-hydroxypyrazole,
2-amino-5-mercapto-1,3,4-thiadiazole,
2-amino-5-methyl-1,3,4-thiadiazole,
2-amino-5-trifluoromethyl-1,3,4-thiadiazole,
2-amino-5-tert.-butyl-1,3,4-thiadiazole,
2-aminopyrazine,
3-amino-2-carboxy-pyrazine,
2-aminopyridazine,
2-aminobenzimidazole,
2-amino-5,6-dimethylbenzimidazole,
5-aminobenzotriazole,
3-amino-7-chloro-1,2,4-benzotriazine,
3-amino-1,2,4-benzotriazine,
3-amino-7-bromo-1,2,4-benzotriazine,
3-amino-7-fluoro-1,2,4-benzotriazine,
3-amino-7-nitro-1,2,4-benzotriazine,
2-aminobenzothiophene,
3-aminobenzothiophene,
4-amino-2,1,3-benzothiadiazole,
3-amino-1,2,4-triazine,
4-amino-2,6-dimercapto-1,3,5-triazine,
3-amino-5,6-dimethyl-1,2,4-triazine,
3-amino-5,6-diphenyl-1,2,4-triazine,
3-amino-5-mercapto-1,2,4-triazole,
4-amino-1,2,4-triazole,
5-aminotetrazole,
5-aminoquinoline,
4-amino-2-methylquinoline,
5-amino-6-nitroquinoline,
8-amino-1,2,3,4-tetrahydroquoline,
2-aminoquinoline,
3-aminoquinoline,
8-aminoquinoline,
8-amino-6-methoxyquinoline,
1-aminoisoquinoline,
5-aminoisoquinoline,
5-aminoindole,
5-aminoindoline,
5-aminoindazole,
3-amino-6-chloroindazole,
6-aminoindazole,
7-aminoindazole,
3-amino-9-ethylcarbazole,
9-amino-tetrahydroacridine,
2-amino-3-hydroxyphenazine and,
2-amino-4-hydroxypteridine.

The benzisoselenazolones of the formula I according to the invention can be converted into pharmaceutical products in a customary manner. In order to produce pharmaceutical products containing benzisoselenazolones of the formula I as the active component, the active ingredient can be employed as such or combined with suitable pharmaceutical diluents and/or vehicles and formulated in a customary manner. The active ingredient can be used in human and veterinary medicine in any desired form, for example systemically, with the proviso that the setting up and maintenance of adequate levels of active ingredient in the blood or tissue is ensured. This can be achieved by oral or rectal or parenteral administration of suitable doses. The pharmaceutical formulation of the active ingredient is advantageously in the form of single doses adjusted to be appropriate for the desired administration, such as, for example, tablets, coated tablets, capsules, suppositories, granules, solutions, emulsions, suspensions, sols or gels. The dosage of the compounds is customarily between 10 and 1,000 mg per day, preferably between 30 and 300 mg, and this can be administered once or several times, preferably two to three times a day.

Examples of vehicles suitable for the production of agents for oral administration, for example in the form of tablets, capsules, granules or powders, are calcium carbonate, calcium phosphate, starch, sugar, lactose, talc, magnesium stearate, gelatine, polyvinylpyrrolidone, gum arabic, sorbitol, microcrystallinecellulose, polyethylene glycol, carboxymethylcellulose, shellac and the like. The tablets can be coated in a customary manner. Liquid formulations for oral administration can be in the form of aqueous or oily suspensions or solutions, in the form of a syrup or of an elixir or the like. These are produced in a customary manner. The injectable formulations can be aqueous or oily suspensions or solutions, or can be powdered compositions with a filler and can be freeze-dried preparations which are dissolved before use or the like. These formulations are produced in a customary manner. The pharmaceutical products according to the invention can also be in the form of suppositories for rectal administration, it being possible for these to contain pharmaceutically tolerated vehicles which are known as such, for example polyethylene glycol, lanolin, cocoa butter, Witepsol® etc. Preparations for external use are preferably produced in the form of ointments or creams which are produced in a customary manner using customary constituents.

The preparation of the compounds according to the invention is illustrated in more detail by the following examples.

EXAMPLE 1

2-(2-pyridyl)-1,2-benzisoselenazol-3(2H)-one, 5.08 g (0.054 mol) of 2-aminopyridine and 16.6 ml (0.12 mol) of triethylamine, dissolved in 120 ml of absolute tetrahydrofuran, are slowly added dropwise, with stirring and cooling in ice (temperature less than 10° C.) under an atmosphere of nitrogen, to a solution of 13.75 g (0.054 mol) of o-chloroselenobenzoyl chloride in 50 ml of absolute tetrahydrofuran. The major part of the solvent is distilled out in vacuo and the residue left behind is poured into ice-water. The insoluble part is filtered off with suction, washed with a large amount of water and recrystallised from dioxane.

Yield: 13.17 g (88.3% of theory), melting point 237°–239° C.

IR (in KBr): 1620 cm$^{-1}$

MS [m/e]: 276 (100%), 196 (42.2%), 168 (30.4%) 156 (34.1%), 138 (16.4%), 78 (15.2%).

EXAMPLE 2

2-(3-hydroxy-2-pyridyl)-1,2-benzisoselenazol-3(2H)-one.

A solution of 4.08 g (0.016 mol) of o-chloroselenobenzoyl chloride in 50 ml of carbon tetrachloride is added dropwise to a vigorously stirred solution of 1.76 g (0.016 mol) of 2-amino-3-hydroxypyridine in 40 ml of carbon tetrachloride and 50 ml of dry pyridine under an atmosphere of nitrogen while cooling in ice (temperature about 5° C). The mixture is stirred at about 10° C. for a further 5 hours. After addition of chloroform, the solution is poured into ice-water. The organic phase is washed several times with water, dried and evaporated. The residue is recrystallised from ethanol.

Yield: 2.86 g (61.3% of theory), melting point 238° C.
IR (in KBr): 1625 cm$^{-1}$
MS [m/e]: 292 (89%), 275 (9.4%), 184 (100%) 156 (35.2%), 108 (10.9%).

EXAMPLE 3

2-(3-sulfolanyl)-1,2-benzisoselenazol-3(2H)-one.

4.1 g (0.03 mol) of 3-aminosulfolane, dissolved in 40 ml of carbon tetrachloride and 40 ml of dry pyridine, are added dropwise, with vigorous stirring and cooling in ice under an atmosphere of nitrogen, to a solution of 2.55 g (0.01 mol) of o-chloroselenobenzoyl chloride in 50 ml of carbon tetrachloride. After stirring for 3 hours, 100 ml of chloroform are added to the mixture and it is extracted by shaking with 100 ml of two normal hydrochloric acid. The organic phase which has been washed with water is evaporated and the residue is recrystallised from ethanol/toluene.

Yield: 1.48 g (66% of theory), melting point 128°–130° C.
IR (in KBr): 1597 cm$^{-1}$
MS [m/e]: 317 (75.7%), 225 (100%), 212 (6.7%), 199 (52.3%), 184 (38.3%), 156 (37.8%), 145 (22.4%), 117 (16.8%).

The following are prepared in analogy to the procedure in Example 1:

EXAMPLE 4

2-(4-pyridyl)-1,2-benzisoselenazol-3(2H)-one.
Yield: 78% of theory, melting point 259°–261° C.
IR (in KBr): 1662 cm$^{-1}$
MS [m/e]: 276 (70.6%), 196 (100%), 184 (7.3%), 168 (14.3%), 156 (18%), 138 (5.8%).

EXAMPLE 5

1-(3-pyridyl)-1,2-benzisoselenazol-3(2H)-one.
Yield: 81% of theory, melting point 265°–267° C.
IR (in KBr): 1635 cm$^{-1}$
MS [m/e]: 276 (77.9%), 196 (100%), 184 (7.6%) 168 (22.8%), 156 (18.8%), 138 (7.7%).

EXAMPLE 6

2-(2-chloro-3-pyridyl)-1,2-benzisoselenazol-3(2H)-one.
Yield: 72% of theory, melting point 199°–201° C.
IR (in KBr): 1666 cm$^{-1}$
MS [m/e]: 310 (25%), 275 (100%), 247 (9.5%), 184 (11.6%), 156 (28%).

EXAMPLE 7

2-(2-pyrimidinyl)-1,2-benzisoselenazol-3(2H)-one.
Yield: 88% of theory, melting point 285° C.
IR (in KBr): 1671 cm$^{-1}$
MS [m/e]: 277 (100%), 235 (7.8%), 197 (19.9%), 184 (16.2%), 169 (23.1%), 156 (42.6%) 117 (7.7%).

EXAMPLE 8

2-(2-thiazolyl)-1,2-benzisoselenazol-3(2H)-one.
Yield: 72% of theory, melting point 288°–290° C.
IR (in KBr): 1658 cm$^{-1}$
MS [m/e]: 282 (85.6%), 234 (12.2%), 202 (18.5%) 184 (100%), 156 (59.5%), 136 (11.6%) 117 (16%).

EXAMPLE 9

2-(benzothiazolyl)-1,2-benzisoselenazol-3(2H)-one.
Yield: 87% of theory, melting point 350° C.
IR (in KBr): 1657 cm$^{-1}$
MS [m/e]: 332 (100%), 252 (39.4%), 224 (12.9%), 184 (67.6%), 156 (62.3%).

EXAMPLE 10

2-(5-chloro-2-pyridyl)-1,2-benzisoselenazol-3(2H)-one.
Yield: 54% of theory, melting point 267°–269° C.
Ir (in KBr): 1612 cm$^{-1}$
MS [m/e]: 310 (100%), 275 (14.63%), 230 (46.80%), 202 (25.85%), 167 (7.65%), 156 (33.75%)

EXAMPLE 11

2-(6-methoxy-3-pyridyl)-1,2-benzisoselenazol-3(2H)-one.
Yield: 45% of theory, melting point 224°–225° C.
IR (in KBr): 1588 cm$^{-1}$
MS [m/e]: 306 (100%), 277 (8.23%), 225 (45.19%) 197 (27.93%), 156 (14.49%), 80 (23.58%).

EXAMPLE 12

2-(2,6-dichloro-3-pyridyl)-1,2-benzisoselenazol-3(2H)-one.
Yield: 38% of theory, melting point 194°–195° C.
IR (in KBr): 1623 cm$^{-1}$
MS [m/e]: 344 (22.0%), 309 (100%), 184 (11.5%), 156 (26.3%)

EXAMPLE 13

2-(4,6-dimethyl-2-pyridyl)-1,2-benzisoselenazol-3(2H)-one.
Yield: 77% of theory, melting point 238°–241° C.
MS [m/e]: 304 (100%), 224 (64.50%), 196 (13.54%) 77 (16.10%).

The following are prepared in analogy to the procedures in Examples 1–3:
2-(6-hydroxy-2-pyridyl)-1,2-benzisoselenazol-3(2H)-one,
2-(3-nitro-2-pyridyl)-1,2-benzisoselenazol-3(2H)-one,
2-(5-nitro-2-pyridyl)-1,2-benzisoselenazol-3(2H)-one,
6-methyl-2-(2-pyridyl)-1,2-benzisoselenazol-3(2H)-one,
6-chloro-2-(2-pyridyl)-1,2-benzisoselenazol-3(2H)-one,
6-methoxy-2-(2-pyridyl)-1,2-benzisoselenazol-3(2H)-one,
5-nitro-2-(2-pyridyl)-1,2-benzisoselenazol-3(2H)-one,
5-chloro-2-(2-pyridyl)-1,2-benzisoselenazol-3(2H)-one,
7-methoxy-2-(2-pyridyl)-1,2--benzisoselenazol-3(2H)-one,
6,7-methylenedioxy-2-(2-pyridyl)-1,2-benzisoselenazol-3(2H)-one,
2-(3-methyl-2-pyridyl)-1,2-benzisoselenazol-3(2H)-one,
2-(4-methyl-2-pyridyl)-1,2-benzisoselenazol-3(2H)-one,
2-(5-methyl-2-pyridyl)-1,2-benzisoselenazol-3(2H)-one,
2-(6-methyl-2-pyridyl)-1,2-benzisoselenazol-3(2H)-one, 2-(3,5-dichloro-2-pyridyl)-1,2-benzisoselenazol-3(2H)-one,
2-(4-chloro-2-pyridyl)-1,2-benzisoselenazol-3(2H)-one,
2-(4-carboxy-5-chloro-2-pyridyl)-1,2-benzisoselenazol-3(2H)-one,
2-(2-tetrahydropyridyl)-1,2-benzisoselenazol-3(2H)-one,
2-(3-carboxy-2-pyridyl)-1,2-benzisoselenazol-3(2H)-one,
2-(4-methyl-2-pyrimidinyl)-1,2-benzisoselenazol-3(2H)-one,
2-(5-nitro-2-pyrimidinyl)-1,2-benzisoselenazol-3(2H)-one,
2-(4,6-dimethyl-2-pyrimidinyl)-1,2-benzisoselenazol-3(2H)-one,
2-(2,6-dimethyl-4-pyrimidinyl)-1,2-benzisoselenazol-3(2H)-one,
2-(5-ethoxy-2-ethylmercapto-4-pyrimidinyl)-1,2-benzisoselenazol-3(2H)-one,
2-(5-ethoxycarbonyl-2-hydroxy-4-pyrimidinyl)-1,2-benzisoselenazol-3(2H)-one,
2-(5-carboxy-4-pyrimidinyl)-1,2-benzisoselenazol-3(2H)-one,
2-(6-chloro-2-methylmercapto-4-pyrimidinyl)-1,2-benzisoselenazol-3(2H)-one,
2-(4-chloro-2-methylmercapto-6-pyrimidinyl)-1,2-benzisoselenazol-3(2H)-one,
2-(4-chloro-6-methyl-2-pyrimidinyl)-1,2-benzisoselenazol-3(2H)-one,
2-(6-chloro-3-nitro-2-pyrimidinyl)-1,2-benzisoselenazol-3(2H)-one,
2-(2-chloro-5-nitro-4-pyrimidinyl)-1,2-benzisoselenazol-3(2H)-one,
2-(4,6-dichloro-2-pyrimidinyl)-1,2-benzisoselenazol-3(2H)-one,
2-(4,6-dichloro-5-pyrimidinyl)-1,2-benzisoselenazol-3(2H)-one,
2-(4,6-dihydroxy-2-pyrimidinyl)-1,2-benzisoselenazol-3(2H)-one,
2-(2,6-dihydroxy-4-pyrimidinyl)-1,2-benzisoselenazol-3(2H)-one,
2-(2,4-dihydroxy-5-pyrimidinyl)-1,2-benzisoselenazol-3(2H)-one,
2-(4,6-dimercapto-2-pyrimidinyl)-1,2-benzisoselenazol-3(2H)-one,
2-(6-hydroxy-2-mercapto-4-pyrimidinyl)-1,2-benzisoselenazol-3(2H)-one,
2-(6-hydroxy-2-methylmercapto-4-pyrimidinyl)-1,2-benzisoselenazol-3(2H)-one,
2-(4-hydroxy-6-methyl-2-pyrimidinyl)-1,2-benzisoselenazol-3(2H)-one,
2-(2-hydroxy-5-methyl-4-pyrimidinyl)-1,2-benzisoselenazol-3(2H)-one,
2-(1-phenylpyrazolo(3,4-d)pyrimidin-4-yl)-1,2-benzisoselenazol-3(2H)-one,
2-(pyrazolo(3,4-d)pyrimidin-4-yl)-1,2-benzisoselenazol-3(2H)-one,
2-(6-hydroxypyrazolo(3,4-d)pyrimidin-4-yl)-1,2-benzisoselenazol-3(2H)-one,
2-(6-mercaptopyrazolo(3,4-d)pyrimidin-4-yl)-1,2-benzisoselenazol-3(2H)-one,
2-(2-hydroxy-4-pyrimidinyl)-1,2-benzisoselenazol-3(2H)-one,
2-(4-chloro-2-benzothiazol)-1,2-benzisoselenazol-3(2H)-one,
2-(4-methoxy-2-benzothiazolyl)-1,2-benzisoselenazol-3(2H)-one,
2-(6-methoxy-2-benzothiazolyl)-1,2-benzisoselenazol-3(2H)-one,
2-(4-methyl-2-benzothiazolyl)-1,2-benzisoselenazol-3(2H)-one,
2-(2-methyl-5-benzothiazolyl)-1,2-benzisoselenazol-3(2H)-one,
2-(6-nitro-2-benzothiazolyl)-1,2-benzisoselenazol-3(2H)-one,
2-(6-bromo-2-benzothiazolyl)-1,2-benzisoselenazol-3(2H)-one,
2-(5,6-dimethyl-2-benzothiazolyl)-1,2-benzisoselenazol-3(2H)-one,
2-(6-ethoxy-2-benzothiazolyl)-1,2-benzisoselenazol-3(2H)-one,
6-methyl-2-(2-thiazolyl)-1,2-benzisoselenazol-3(2H)-one,
6-chloro-2-(2-thiazolyl)-1,2-benzisoselenazol-3(2H)-one,
6-methoxy-2-(2-thiazolyl)-1,2-benzisoselenazol-3(2H)-one,
5-nitro-2-(2-thiazolyl)-1,2-benzisoselenazol-3(2H)-one,
5-chloro-2-(2-thiazolyl)-1,2-benzisoselenazol-3(2H)-one,
7-methoxy-2-(2-thiazolyl)-1,2-benzisoselenazol-3(2H)-one,
6,7-methylenedioxy-2-(2-thiazolyl)-1,2-benzisoselenazol-3(2H)-one,
2-(4-methyl-2-thiazolyl)-1,2-benzisoselenazol-3(2H)-one,
2-(5-nitro-2-thiazolyl)-1,2-benzisoselenazol-3(2H)-one,
2-(2-thiazolinyl)-1,2-benzisoselenazol-3(2H)-one,
2-(5-chloro-2-thiazolyl)-1,2-benzisoselenazol-3(2H)-one,
2-(3-methyl-5-isothiazolyl)-1,2-benzisoselenazol-3(2H)-one,
2-(2-imidazolyl)-1,2-benzisoselenazol-3(2H) one,
2-(5-ethoxycarbonyl-2-imidazolyl)-1,2-benzisoselenazol-3(2H)-one,
2-(3-pyrazolyl)-1,2-benzisoselenazol-3(2H)-one,
2-(4-cyano-5-pyrazolyl)-1,2-benzisoselenazol-3(2H)-one,
2-(4-ethoxycarbonyl-3-pyrazolyl)-1,2-benzisoselenazol-3(2H)-one,
2-(4-ethoxycarbonyl-2-phenyl-3-pyrazolyl)-1,2-benzisoselenazol-3(2H)-one,
2-(4-cyano-3-pyrazolyl)-1,2-benzisoselenazol-3(2H)-one,
2-(2-phenyl-3-pyrazolyl)-1,2-benzisoselenazol-3(2H)-one,
2-(1-phenyl-5-pyrazolyl)-1,2-benzisoselenazol-3(2H)-one,
2-(1-phenyl-5-pyrazolon-3-yl)-1,2-benzisoselenazol-3(2H)-one,
2-(5-hydroxy-3-pyrazolyl)-1,2-benzisoselenazol-3(2H)-one,
2-(1,3,4-thiadiazol-2-yl)-1,2-benzisoselenazol-3(2H)-one,
2-(5-mecapto-1,3,4-thiadiazol-2-yl)-1,2-benzisoselenazol-3(2H)-one,
2-(5-methyl-1,3,4-thiadiazol-2-yl)-1,2-benzisoselenazol-3(2H)-one,
2-(5-trifluoromethyl-1,3,4-thiadiazol-2-yl)-1,2-benzisoselenazol-3(2H)-one,
2-(5-tert.-butyl-1,3,4-thiadiazol-2-yl)-1,2-benzisoselenazol-3(2H)-one,
2-(2-pyrazinyl)-1,2-benzisoselenazol-3(2H)-one,
2-(2-carboxy-3-pyrazinyl)-1,2-benzisoselenazol-3(2H)-one, 2-(2-pyridazinyl)-1,2-benzisoselenazol-3(2H)-one,
2-(2-benzimidazolyl)-1,2-benzisoselenazol-3(2H)-one,
2-(5,6-dimethyl-2-benzimidazolyl)-1,2-benzisoselenazol-3(2H)-one,
2-(5-benzotriazolyl)-1,2-benzisoselenazol-3(2H)-one,
2-(7-chloro-1,2,4-benzotriazin-3-yl)-1,2-benzisoselenazol-3(2H)-one,
2-(1,2,4-benzotriazin-3-yl)-1,2-benzisoselenazol-3(2H)-one,
2-(7-bromo-1,2,4-benzotriazin-3-yl)-1,2-benzisoselenazol-3(2H)-one,
2-(7-fluoro-1,2,4-benzotriazin-3-yl)-1,2-benzisoselenazol-3(2H)-one,
2-(7-nitro-1,2,4-benzotriazin-3-yl)-1,2-benzisoselenazol-3(2H)-one,
2-(2-benzothienyl)-1,2-benzisoselenazol-3(2H)-one,
2-(3-benzothienyl)-1,2-benzisoselenazol-3(2H)-one,
2-(2-thienyl)-1,2-benzisoselenazol-3(2H)-one,
2-(2,1,3-benzothiadiazol-4-yl)-1,2-benzisoselenazol-3(2H)-one,
2-(1,2,4-triazin-4-yl)-1,2-benzisoselenazol-3(2H)-one,
2-(2,6-dimercapto-1,3,5-triazin-4-yl)-1,2-benzisoselenazol-3(2H)-one,
2-(5,6-dimethyl-1,2,4-triazin-3-yl)-1,2-benzisoselenazol-3(2H)-one,
2-(5,6-diphenyl-1,2,4-triazin-3-yl)-1,2-benzisoselenazol-3(2H)-one,
2-(1,2,4-triazol-4-yl)-1,2-benzisoselenazol-3(2H)-one,
2(5-mercapto-1,2,4-triazol-3-yl)-1,2-benzisoselenazol-3(2H)-one,
2-(5-tetrazolyl)-1,2-benzisoselenazol-3(2H)-one,
2-(5-quinolyl)-1,2-benzisoselenazol-3(2H)-one,
2-(2-methyl-4-quinolyl)-1,2-benzisoselenazol-3(2H)-one,
2-(6-nitro-5-quinolyl)-1,2-benzisoselenazol-3(2H)-one,
2-(1,2,3,4-tetrahydroquinol-8-yl)-1,2-benzisoselenazol-3(2H)-one,
2-(2-quinolyl)-1,2-benzisoselenazol-3(2H)-one,
2-(3-quinolyl)-1,2-benzisoselenazol-3(2H)-one,
2-(8-quinolyl)-1,2-benzisoselenazol-3(2H)-one,
2-(6-methoxy-8-quinolyl)-1,2-benzisoselenazol-3(2H)-one,
2-(1-isoquinolyl)-1,2-benzisoselenazol-3(2H)-one,
2-(5-isoquinolyl)-1,2-benzisoselenazol-3(2H)-one,
2-(5-indolyl)-1,2-benzisoselenazol-3(2H)-one,
2-(5-isoindoyl)-1,2-benzisoselenazol-3(2H)-one,
2-(5-indazolyl)-1,2-benzisoselenazol-3(2H)-one,
2-(6-chloro-3-indazolyl)-1,2-benzisoselenazol-3(2H)one,
2-(6-indazolyl)-1,2-benzisoselenazol-3(2H)-one,
2-(7-indazolyl)-1,2-benzisoselenazol-3(2H)-one,
2-(9-ethyl-3-carbazolyl)-1,2-benzisoselenazol-3(2H)-one,
2-(9-tetrahydroacridinyl)-1,2-benzisoselenazol-3(2H)-one,
2-(3-hydroxy-2-phenazinyl)-1,2-benzisoselenazol-3(2H)-one, and
2-(4-hydroxy-2-pteridinyl)-1,2-benzisoselenazol-3(2H)-one.

What we claim is:

1. Benzisoselenazolones of the formula I

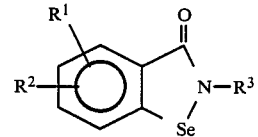

wherein $R^1$ and $R^2$ which can be the same or different from each other, are selected from the group consisting of hydrogen, halogen, $C_1$–$C_4$-alkyl, $C_1$–$C_4$-alkoxy, hydroxyl, trifluoromethyl, nitro, di-($C_1$–$C_4$-alkyl)-amino and $R^1$ and $R^2$ together, methylenedioxy, and $R^3$ is a member selected from the group consisting of the heterocyclic group pyridyl, and such heterocyclic group substituted once or twice, identically or differently, by halogen, $C_1$–$C_2$-alkyl, $C_1$–$C_4$-alkoxy, hydroxyl, nitro, and carboxyl.

2. Benzisoselenazolones according to claim 1, wherein $R^1$ and $R^2$ which can be identical or different from each other, are members selected from the group consisting of hydrogen, fluorine, chlorine, bromine, hydroxyl, methoxy, trifluoromethyl, nitro and, $R^1$ and $R^2$ together, methylendioxy, and $R^3$ is a member selected from the group consisting of the cyclic group pyridyl, and such heterocyclic group substituted once or twice, identically or differently, by fluorine, chlorine, bromine, methyl, ethyl, butyl, methoxy, ethoxy, hydroxyl, nitro, carboxyl.

3. Benzisoselenazolones according to claim 1, wherein $R^1$ and $R^2$ which can be identical or different from each other are selected from the group consisting of hydrogen, chlorine, methyl, methoxy, nitro and $R^1$ and $R^2$ together, methylenedioxy, and $R^3$ is a member selected from the group consisting of the heterocyclic group, pyridyl, and such heterocyclic group substituted once or twice, identically or differently, by fluorine, chlorine, bromine, methyl, methoxy, ethoxy, hydroxyl, nitro, carboxyl.

4. 2-(2-Pyridyl)-1,2-benzisoselenazol-3(2H)-one.
5. 2-(3-Pyridyl)-1,2-benzisoselenazol-3(2H)-one.
6. 2-(4-Pyridyl)-1,2-benzisoselenazol-3(2H)-one.
7. 2-(2-Chloro-3-pyridyl)-1,2-benzisoselenazol-3(2H)-one.
8. 2-(2,6-Dichloro-3-pyridyl)-1,2-benzisoselenazol-3(2H)-one.
9. 2-(6-Methoxy-3-pyridyl)-1,2-benzisoselenazol-3(2H)-one.
10. 2-(5-Chloro-2-pyridyl)-1,2-benzisoselenazol-3(2H)-one.
11. 2-(4,6-Dimethyl-2-pyridyl)-1,2-benzisoselenazol-3(2H)-one.

* * * * *